(12) United States Patent
Barak (10) Patent No.: US 8,966,788 B2
(45) Date of Patent: Mar. 3, 2015

(54) SET OF PODIATRIC ARTICLES

(76) Inventor: Yehushua Barak, Holon (IL)

( * ) Notice: Subject to any disclaimer, the term of this patent is extended or adjusted under 35 U.S.C. 154(b) by 865 days.

(21) Appl. No.: 13/048,947

(22) Filed: Mar. 16, 2011

(65) Prior Publication Data

US 2012/0233889 A1 Sep. 20, 2012

(51) Int. Cl.
*A43B 7/14* (2006.01)
*A61F 5/14* (2006.01)

(52) U.S. Cl.
CPC .......................................... *A61F 5/14* (2013.01)
USPC .................................................. 36/92; 36/173

(58) Field of Classification Search
USPC ................................................ 36/92, 80, 173
See application file for complete search history.

(56) References Cited

U.S. PATENT DOCUMENTS

| | | | | |
|---|---|---|---|---|
| 2,031,510 A | * | 2/1936 | Stewart et al. | 36/176 |
| 2,260,377 A | * | 10/1941 | Herbst | 36/80 |
| 2,637,122 A | * | 5/1953 | Baer | 36/173 |
| 2,828,555 A | * | 4/1958 | Ledos | 36/176 |
| 4,084,333 A | * | 4/1978 | Del Vecchio | 36/43 |
| 4,266,553 A | * | 5/1981 | Faiella | 36/144 |
| 4,686,993 A | * | 8/1987 | Grumbine | 36/140 |
| 4,862,604 A | * | 9/1989 | Hauser | 36/43 |
| 6,247,250 B1 | * | 6/2001 | Hauser | 36/44 |
| 6,315,786 B1 | * | 11/2001 | Smuckler | 606/201 |
| 7,426,794 B2 | * | 9/2008 | Swensen | 36/43 |

* cited by examiner

*Primary Examiner* — Marie Bays
(74) *Attorney, Agent, or Firm* — The Law Office of Michael E. Kondoudis (57) ABSTRACT

A set of podiatric articles each of which is placeable into a respective one of a pair of shoes. Each article includes: an arch area with a cross-sectional profile; and a heel area having a depth D and a concave shape that provides a round recess that is adapted to accept a heel. The arch areas of the respective articles of the set share a same cross-sectional profile. The heel areas of the respective articles of the set have different depths D so that the heel is differently suspended from a bottom of the heel area. The arch area and the heel area are adapted, configured and cooperate to suspend the heel within the heel area so that the heel is not in contact with the article and a calcaneal spur of the heel is spacedly disposed from a bottom of the recess of the heel area.

8 Claims, 10 Drawing Sheets

SET OF PODIATRIC ARTICLES

FIELD OF THE INVENTION

The present invention relates to an articles, and, more specifically, to a set of podiatric articles in which an adequate article is selectable by a patient in a non clinical setting.

BACKGROUND OF THE INVENTION

Orthotic devices have long been employed with considerable success to treat conditions or otherwise enhance the functions of the human foot, whether for ordinary walking or for various forms of specialized activities, such as skiing, skating, running and so on.

U.S. Pat. No. 7,124,518 discloses an orthotic insert assembly having a stationary heel post with a guide slot and an unattached rigid plate member with a depending peg that is received in the slot. The peg cooperates with the guide slot to control and direct a medial-to-lateral rocking movement of the plate member as the wearer's foot progresses through the gait cycle. The slot may be angled to impose a predetermined direction on the rocking movement.

IL Patent 94491 discloses a pair of complementary shoes and 3 pairs of insoles suitable different feet profile. The customer can select an adequate pair of insoles in a non clinical setting.

The cited patent documents do not solve the problem of acquisition and selection of an adequate podiatric article without intervention of a physician, an orthopedist or another health care worker. The aforesaid activity extraneous to health care facility is very important to a person with limited motion activity. Thus, there is an unmet and long-felt need to provide a podiatric article placeable into an shoe empirically selectable on the base of patient's maximal comfort and lowest painfulness at home.

SUMMARY OF THE INVENTION

It is hence one object of the invention to disclose a set of podiatric articles placeable into a shoe. Each podiatric article comprises a heel area. The heel area is configured into an anatomically conformed concave shape provided with a recess of preferably circular or oval form such that the patient's calcaneal spur is minimally traumatized.

It is a core purpose of the invention to provide the set further comprising a plurality of podiatric articles characterized by different depth M of said recess to provide maximal comfort and least pain by means of empirical selection by the patient of an appropriate podiatric article in a non-clinical setting.

Another object of the invention is to disclose the set comprising the podiatric articles provided with an arch support area.

A further object of the invention is to disclose the set comprising the podiatric articles provided with a forefoot area.

A further object of the invention is to disclose the article integrated with said shoe.

A further object of the invention is to disclose the least pain is characterized by 0 to 2 pain rating according to Wong-Baker pain scale or any other corresponding level of conventional pain or comfort scale.

A further object of the invention is to disclose the set comprising at least three podiatric articles characterized by said depth M ranged between about 10 and about 35 mm.

A further object of the invention is to disclose the three podiatric articles characterized by said depth M of about 10, about 20 and about 35 mm, respectively.

A further object of the invention is to disclose the set of podiatric articles placeable into a shoe of a standard size according to International Standard is ISO 9407:1991 or any national standard.

A further object of the invention is to disclose a method of using a set of podiatric articles placeable into a shoe. The aforesaid method comprising the steps of: (a) providing the set of podiatric articles; each podiatric article comprises and a heel area; the heel area is configured into an anatomically conformed concave shape provided with a recess of preferably circular or oval form such that the patient's calcaneal spur is minimally traumatized; (b) selecting the appropriate article; (c) using the selected article.

It is a core purpose of the invention to provide the step selecting articles performed in a non clinical setting. The step of selecting the articles comprises selecting the appropriate article amongst the set of podiatric articles characterized by different depth of the recess such that the appropriate article is selectable by means of empiric selection of an adequate podiatric article based on maximal comfort and lowest painfulness criteria.

A further object of the invention is to disclose the step of selecting articles performed according to pain criterion 0 to 2 pain rating of Wong-Baker pain scale or any other corresponding level of conventional pain or comfort scale.

A further object of the invention is to disclose the step of selecting articles performed between at least three podiatric articles characterized by said depth M ranged between about 10 and about 35 mm.

A further object of the invention is to disclose the step of selecting articles performed between said three podiatric articles characterized by said depth M of about 10, about 20 and about 35 mm, respectively.

A further object of the invention is to disclose a method of delivering podiatric articles useful for minimally traumatizing of the patient's calcaneal spur. Each podiatric article comprises a heel area. The heel area is configured into an anatomically conformed concave shape provided with a recess of preferably circular or oval form. The method comprises the steps of: (a) producing said podiatric articles; and (b) preparing for delivering to a patient.

It is a core purpose of the invention to provide the step preparing said set of produced podiatric articles comprises grouping said podiatric articles into identical sets. Each set includes a plurality of podiatric articles characterized by different depth of said recess such that an appropriate article is selectable by means of empiric selection based on maximal comfort and lowest painfulness criterion.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which.

DETAILED DESCRIPTION OF THE INVENTION

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a set of podiatric articles placeable into a shoe and methods of using and delivering the same.

A pain scale measures a patient's pain intensity or other features. Pain scales are based on self-report, observational (behavioral), or physiological data. Self-report is considered primary and should be obtained if possible. Pain scales are available for neonates, infants, children, adolescents, adults, seniors, and persons whose communication is impaired. In accordance with Wong Baker Pain Scale, feeling of the person is characterized by a symbolic face. Specifically, face 0 is very happy because he is not in pain. Face 1 hurts just a little bit. Face 2 hurts a little more. Face 3 hurts even more. Face 4 hurts a lot. Face 5 hurts as much as you can imagine, although you do not have to be crying to feel this bad. The person is asked to choose the face that best describes how he is feeling.

A heel spur is an osteophytic proliferation just anterior to the calcaneal tuberosity that extends plantarly along its entire width. The boney prominence develops and points distally at the attachment of the plantar aponeurosis. The condition may be asymptomatic or may result in painful ambulation.

The patient usually presents with a complaint of pain located mainly under the medial plantar aspect of the heel. The onset is ordinarily gradual, the pain being most intense in the morning upon taking the first steps of the day, decreasing slightly after a period of ambulation, and then becoming more pronounced at day's end.

In addition, the patient may relate a history of increased pain upon ambulation after periods of non-weightbearing. The condition is rarely totally disabling, although a limp may be present. There is normally no history of preceding illness or trauma to the area, and the condition may be present from a few days to a few months before a patient seeks treatment.

It is evident that the major factor in the cause of heel spurs is undoubtedly mechanical, rather than infectious. A heel spur is generally thought to develop from traction on the periosteum that causes consequent subperiosteal ossification. By controlling pronation and lessening the bowstring effect of the plantar aponeurosis, the reactive force will be removed, and the inflammation should subside.

It should be noted that there are heel spurs caused by various infectious and arthritic conditions as well. Some of these conditions are rheumatic and psoriatic arthritis, ankylosing spondylitis, Reiter's syndrome, and Strumpell-Marie disease. However, these cases have been found to be the exception, rather than the rule, as far as etiology is concerned.

There are three types of heel spurs:

I. Those that are large in size but asymptomatic because the angle of growth is such that the spur does not become a weightbearing point, and/or the inflammatory changes have been arrested. This type is usually found incidentally when the foot is X-rayed for some other purpose.

II. Those that are large in size and painful upon weightbearing, because the pitch of the calcaneus has been altered by a depression of the longitudinal arch, and as a result, the spur becomes a weightbearing point, sometimes causing intractable pain.

III. Those that exhibit only a rudimentary proliferation and whose outline is irregular and jagged. These usually are accompanied by an area of decreased density around the origin of the plantar fascia, indicating a subacute inflammatory process. All calcaneal spurs undoubtedly begin in this manner, but only a few become symptomatic at this stage, because in only these few are the etiologic factors acute.

The primary symptom is severe pain in the entire plantar surface of the heel with poststatic dyskinesia. Pinpoint palpation usually elicits maximum pain in the area of the medial tubercle of the calcaneus.

When taking X-rays, one should always take bilateral weightbearing lateral views. In evaluating the X-rays, one must also take into consideration the pathological processes of early fibrosis, osteophytic deposits, and eventual calcification. From our study and those of others, it is evident that a spur need not be evident on X-ray for the heel-spur syndrome to exist.

In the purpose of the current invention, a value M refers both to a dimension of heel projection 110a/110b/110c of the molding model and depth of heel 210a/210b/210c.

Figure 1A:
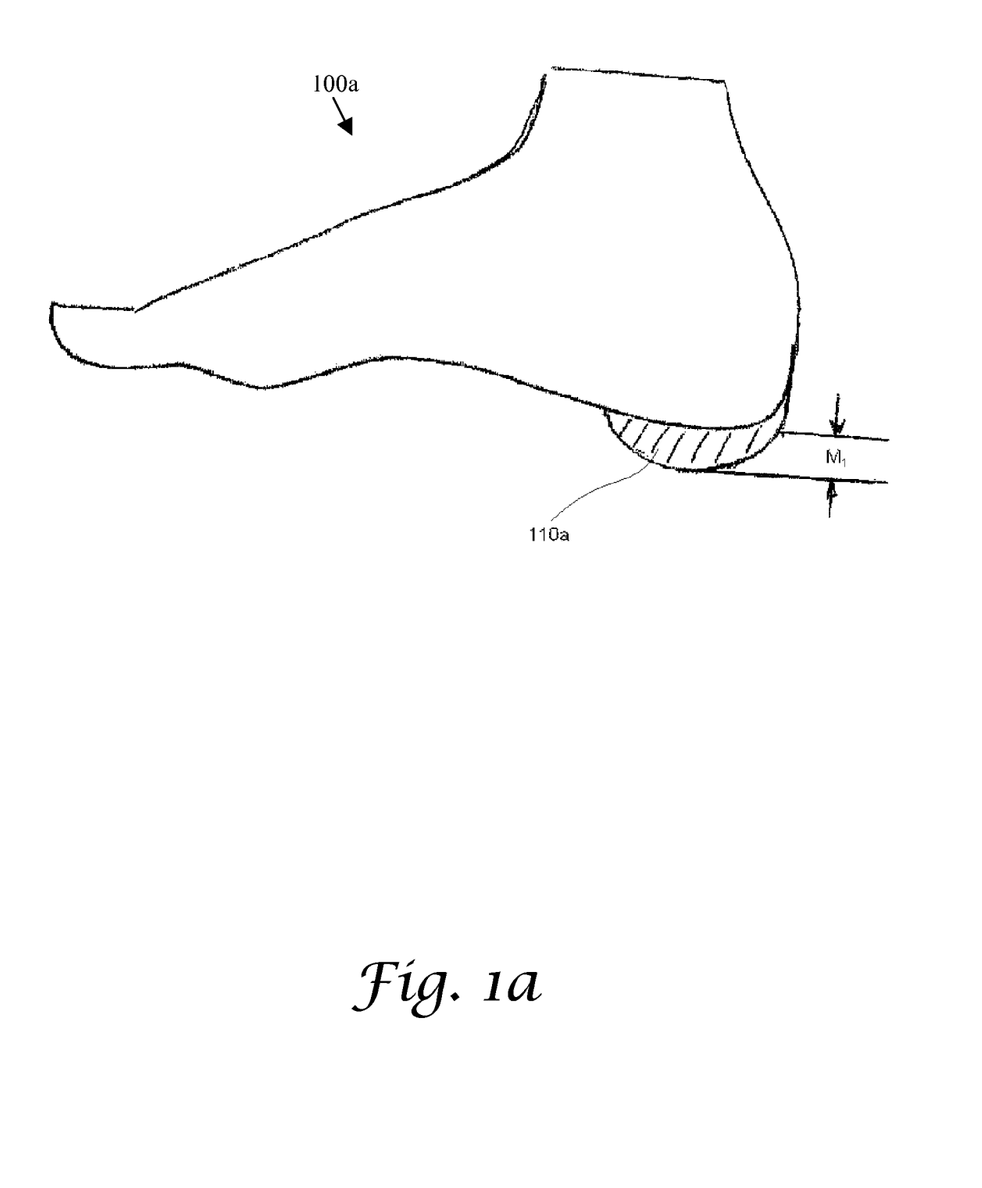
FIGS. 1a to 1c are schematic views of the molding models.
Figure 1B:
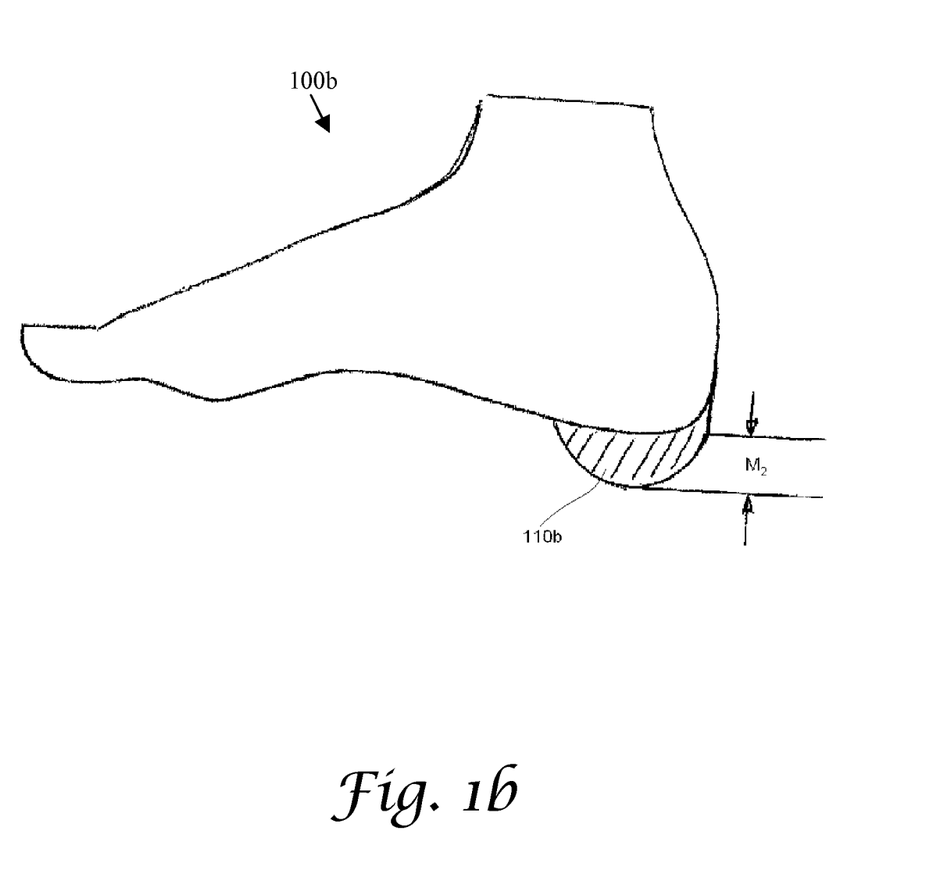
Figure 1C:
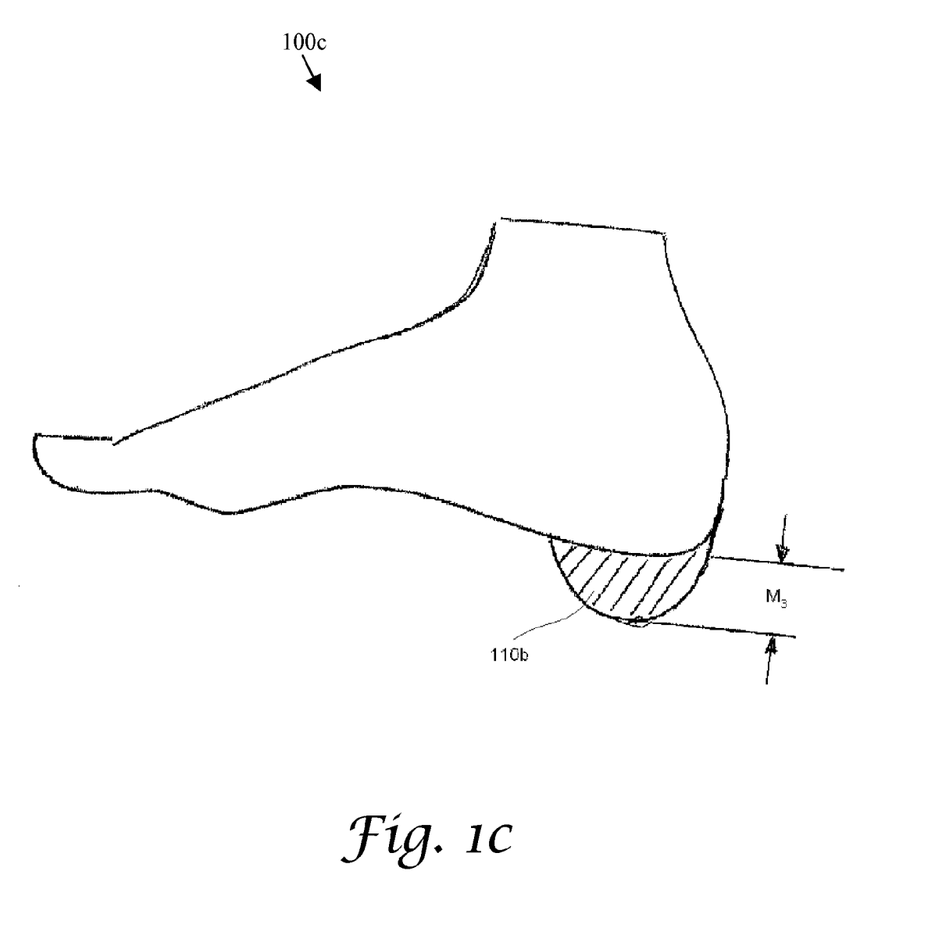

Reference is now made to FIGS. 1a to 1c presenting a set of molding models 100a to 100c having a projection 110a/110b/110c of different dimensions $M_1/M_2/M_3$ adapted for molding the proposed podiatric articles. In accordance with an exemplar non-limiting embodiment, Values of $M_1$, $M_2$ and $M_3$ are equal to 10, 20 and 35 mm.

Figure 2A:
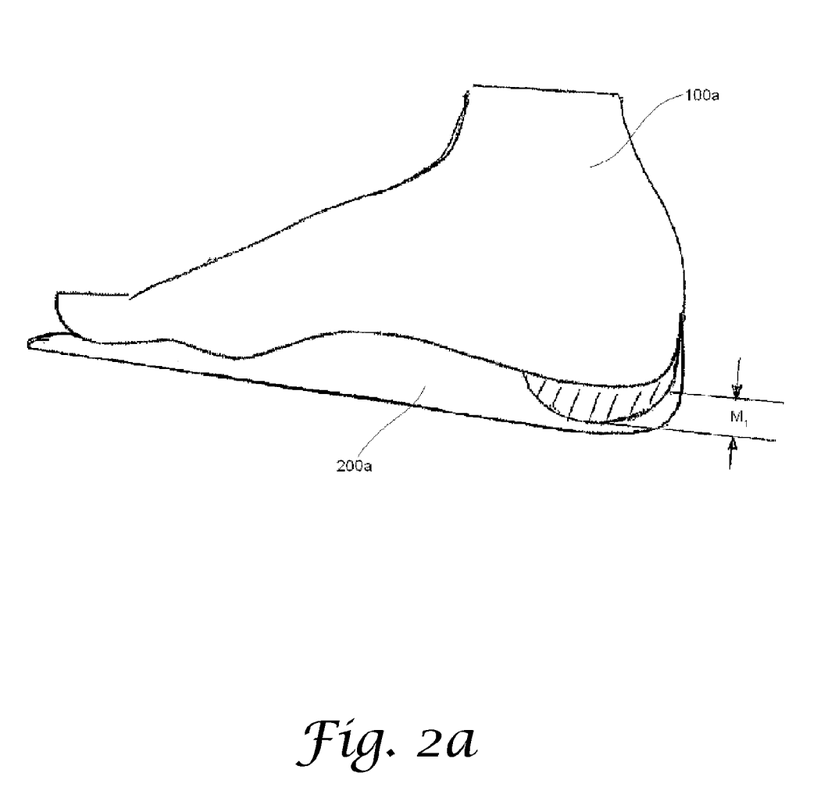
FIGS. 2a to 2c are schematic views of molding models and molded podiatric articles.
Figure 2B:
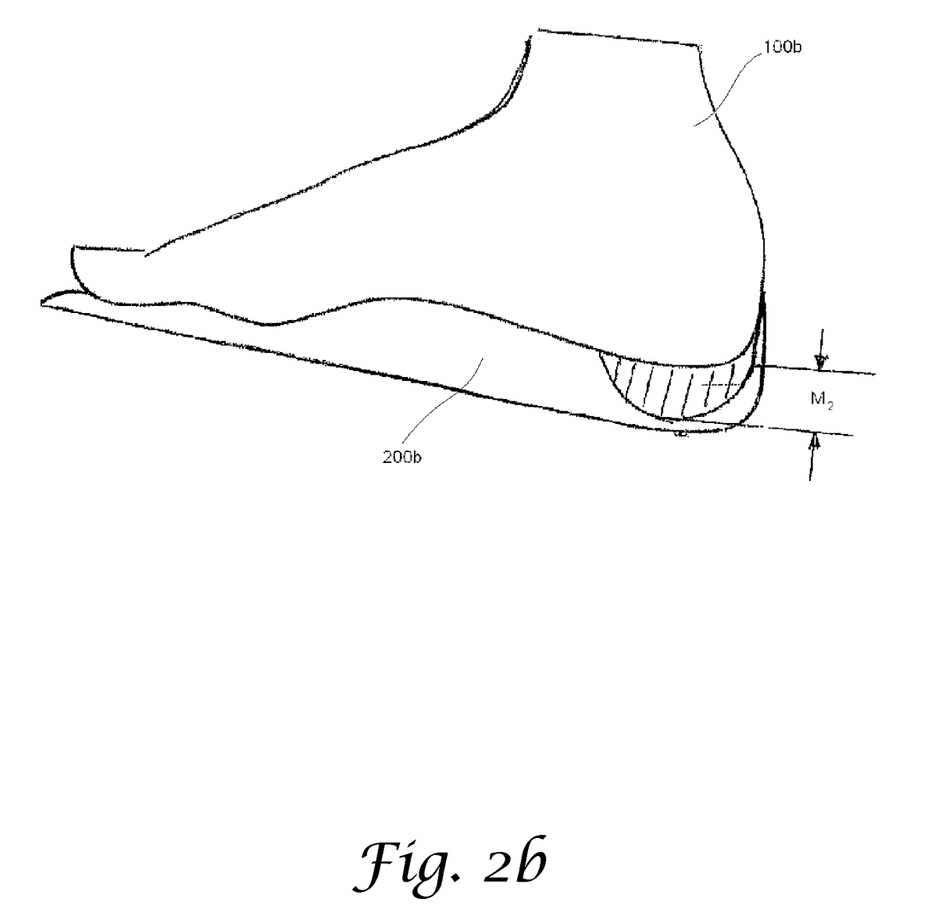
Figure 2C:
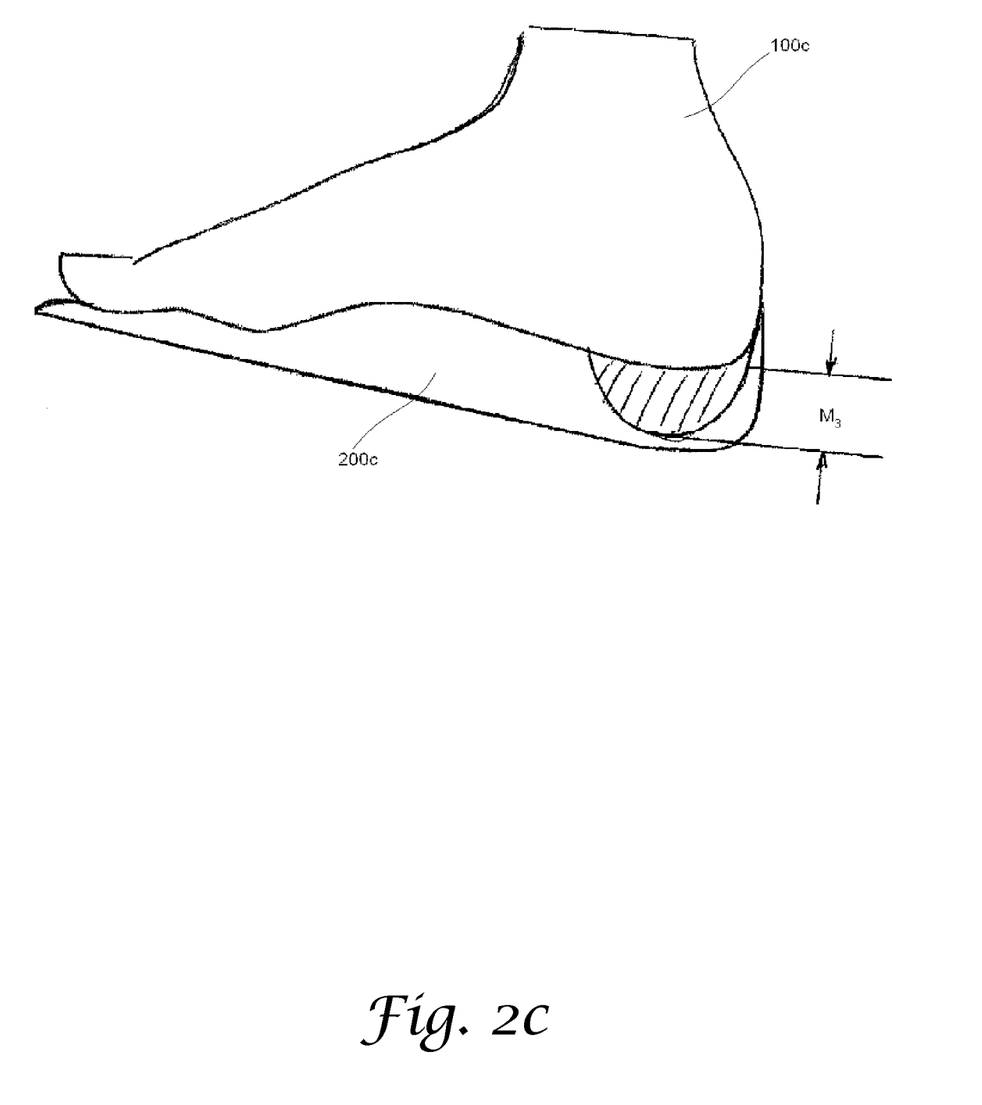

Reference is now made to FIGS. 2a to 2c presenting the molding models 100a/100b/100c and podiatric articles 200a/200b/200c molded thereon. The size-varied models 100a/100b/100c are designed for producing a set of podiatric articles 200a/200b/200c.

Figure 3:
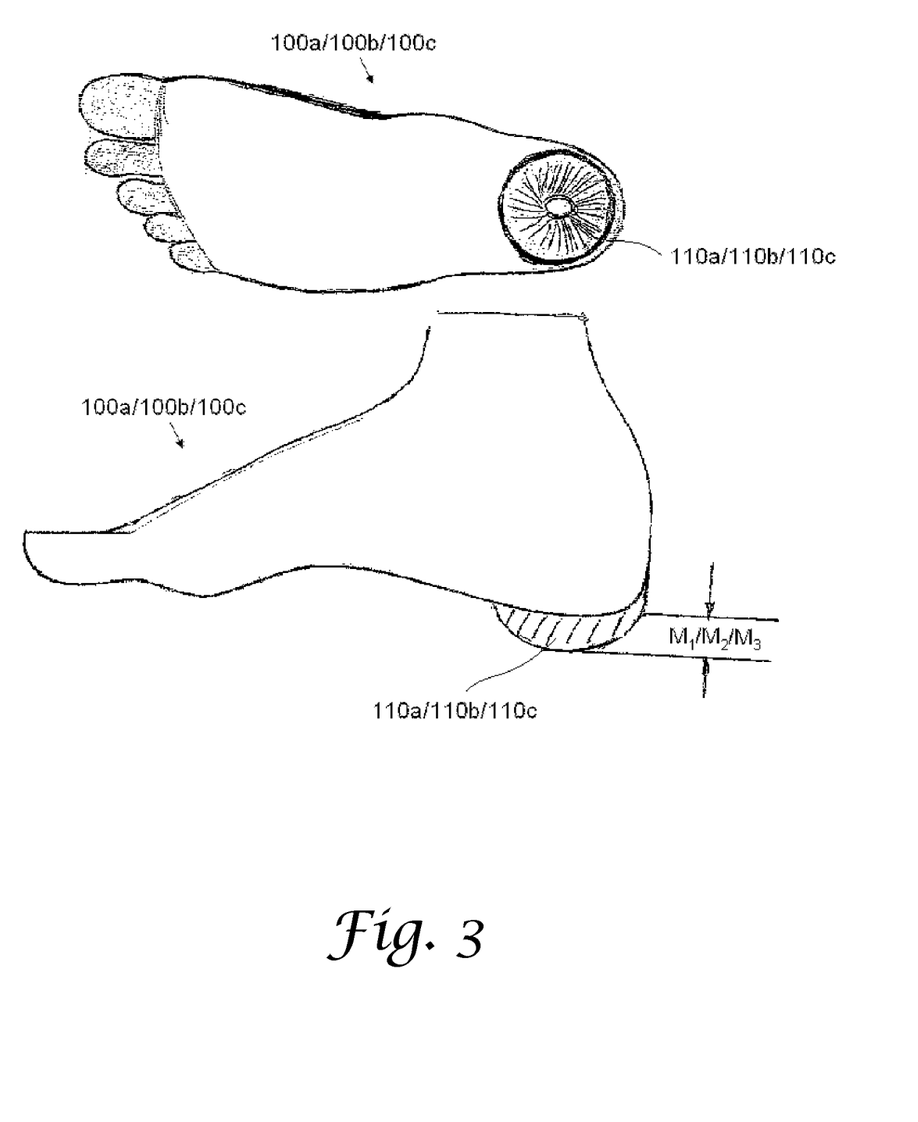
FIG. 3 includes schematic bottom and side views of the molding model.

Reference is now made of FIG. 3 showing bottom and side views of the molding model 100a/100b/100c.

Figure 4A:
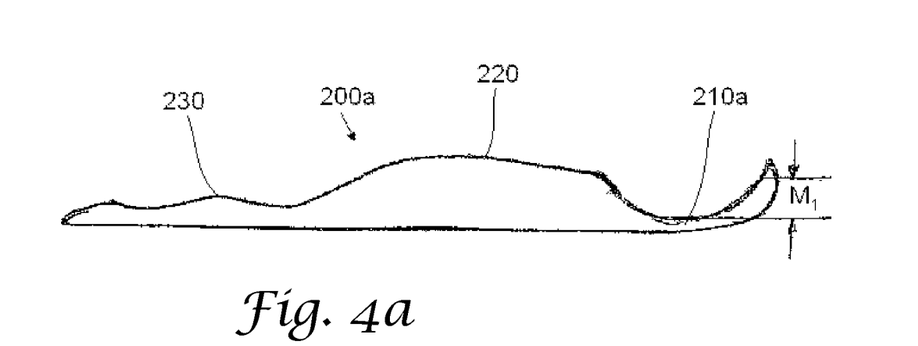
FIGS. 4a to 4c are schematic views of the completed podiatric articles in accordance with the first embodiment of the current invention.
Figure 4B:
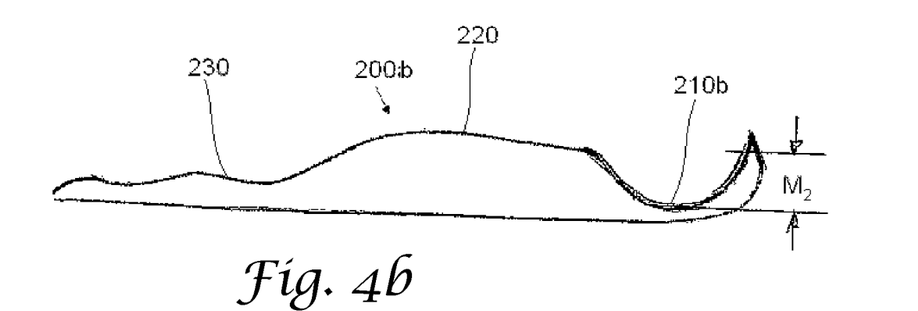
Figure 4C:
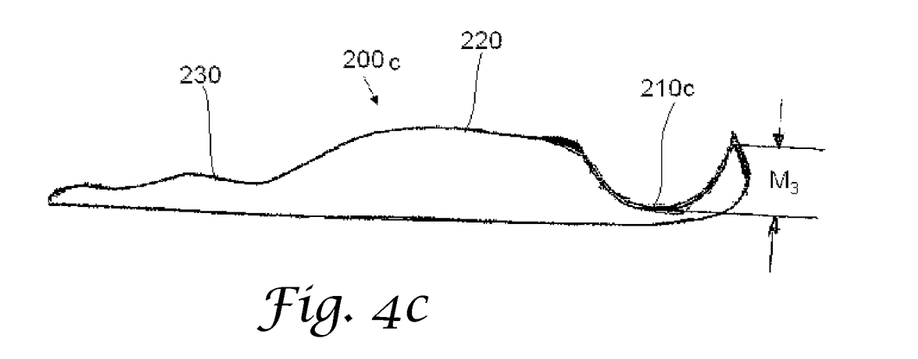

Reference is now made to FIGS. 4a to 4c, presenting a set of the podiatric article 200a/200b/200c (insole) having comprises a forefoot area 230, an arch support area 220 and a heel area 210a/210b/210c. In accordance with the current invention, the patient is provided with a set comprising a number of the aforesaid podiatric articles characterized by a different depth $M_1/M_2/M_3$ (10/20/35 mm) of the heel area 210a/210b/210c molded on the corresponding models 100a/100b/100c, respectively. The patient is able to buy the proposed set in an aids shop and select an appropriate podiatric article at home in conditions which are most comfortable for him/her. A selection criterion is maximal comfort and least pain perceptible by the patient during ambulation. Additionally, in accordance with the proposed solution, there is no chance of inappropriate selection because the patient is able at any time replace the selected article with a more comfortable to him/her podiatric article of the bought set. The selected podiatric article is placed into a shoe of the patient.

Figure 5A:
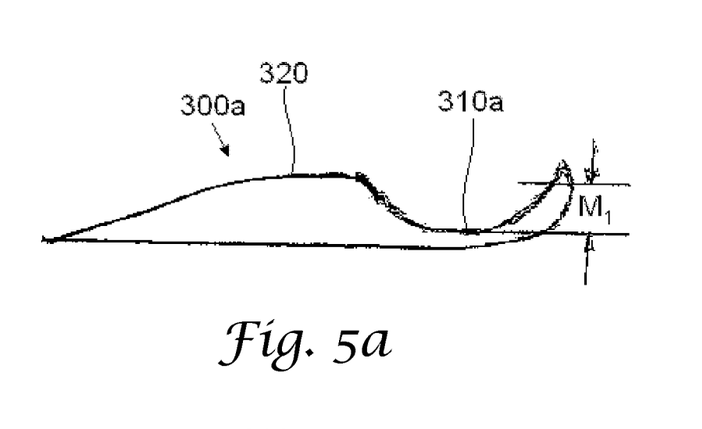
FIGS. 5a to 5c are schematic views of the podiatric articles in accordance with the second embodiment of the current invention.
Figure 5B:
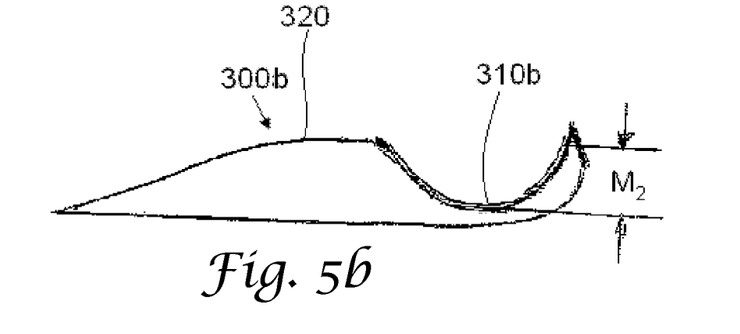
Figure 5C:
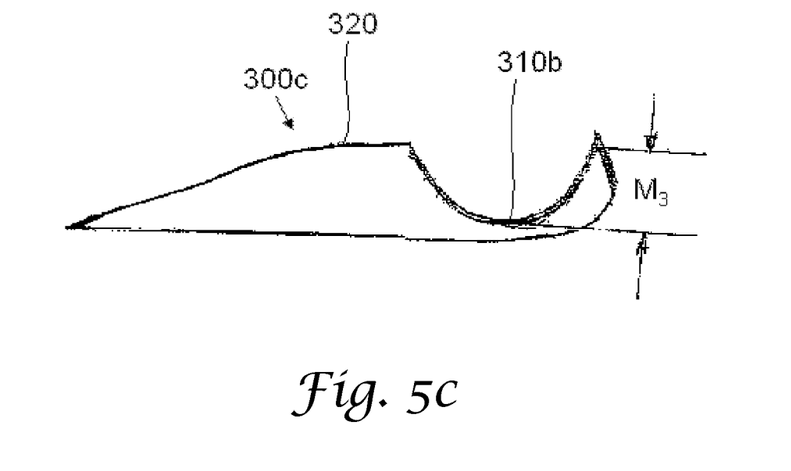

Reference is now made to FIGS. 5a to 5c, presenting a set of reduced podiatric articles 300a/300b/300c comprising recesses 310a/310b/310c and an arch support area 320.

Figure 6A:
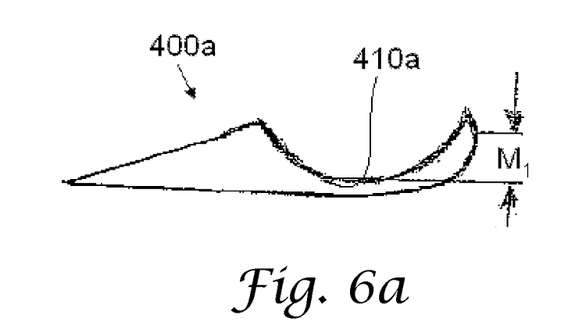
FIGS. 6a to 6c are schematic views of the alternative embodiments of the podiatric articles in accordance with the third embodiment of the current invention.
Figure 6B:
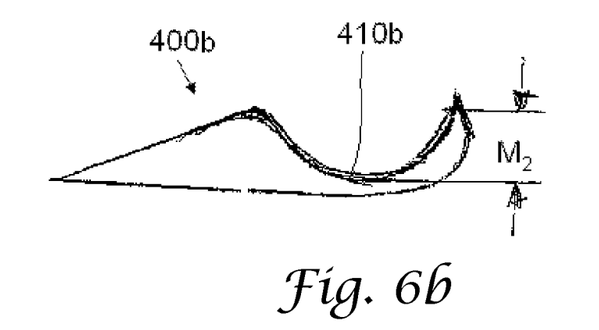
Figure 6C:
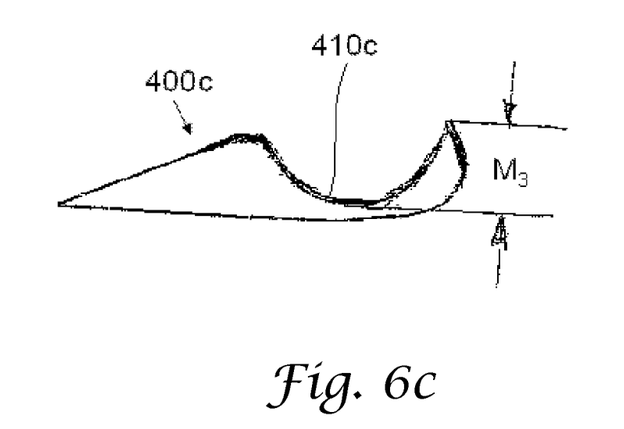

Reference is now made to FIGS. 6a to 6c, presenting a set of reduced podiatric articles 400a/400b/400c comprising recesses 310a/310b/310c.

In accordance with the current invention, a set of podiatric articles placeable into a shoe is disclosed. Each podiatric article comprises a heel area. The heel area is configured into an anatomically conformed concave shape provided with a recess of preferably circular or oval form such that the patient's calcaneal spur is minimally traumatized.

The core feature of the current invention is to provide the set further comprising a plurality of podiatric articles characterized by different depth M of said recess to provide maximal comfort and least pain by means of empirical selection by the patient of an appropriate podiatric article in a non clinical setting.

In accordance with one embodiment of the current invention, the set comprises the podiatric articles provided with an arch support area.

In accordance with another embodiment of the current invention, the set comprises the podiatric articles provided with a forefoot area.

In accordance with another embodiment of the current invention, the article is integrated with said shoe.

In accordance with another embodiment of the current invention, the least pain is at 0 to 2 pain rating according to the Wong-Baker pain scale.

In accordance with a further embodiment of the current invention, the set comprises at least three podiatric articles characterized by said depth M ranged between about 10 and about 35 mm.

In accordance with a further embodiment of the current invention, the three podiatric articles are characterized by said depth M of about 10, about 20 and about 35 mm, respectively.

In accordance with a further embodiment of the current invention, the podiatric articles of set are placeable into a shoe of a standard size according to International Standard is ISO 9407:1991 or any national standard.

In accordance with a further embodiment of the current invention, a method of using a set of podiatric articles placeable into a shoe is disclosed. The aforesaid method comprises the steps of: (a) providing the set of podiatric articles; each podiatric article comprises a heel area; the heel area is configured into an anatomically conformed concave shape provided with a recess of preferably circular or oval form such that the patient's calcaneal spur is minimally traumatized; (b) selecting the appropriate article; (c) using the selected article.

Another core feature of the current invention is to provide the step selecting articles performed in a non clinical setting. The step comprises selecting the appropriate article amongst the set of podiatric articles characterized by different depth M of the recess such that the appropriate article is selectable by means of empiric selection of an adequate podiatric article based on maximal comfort and lowest painfulness criteria.

In accordance with a further embodiment of the current invention, a method of delivering podiatric articles useful for minimally traumatizing of the patient's calcaneal spur is disclosed. Each podiatric article comprises a heel area; said heel area configured into an anatomically conformed concave shape provided with a recess of preferably circular or oval form. The method comprises the steps of: (a) producing said podiatric articles; and (b) preparing for delivering to a patient.

A further core feature of the current invention is to provide the step preparing the produced podiatric articles comprising grouping said podiatric articles into identical sets.

Each set includes a plurality of podiatric articles characterized by different depth M of the recess such that an appropriate article is selectable by means of empiric selection based on maximal comfort and lowest painfulness criterion.

The invention claimed is:

1. A set of podiatric articles each of which is placeable into a respective one of a pair of shoes, each article of the set comprising:
    an arch area with a cross-sectional profile; and
    a heel area having a depth D and a concave shape that provides a round recess that is adapted, configured, and dimensioned to accept a heel;
    wherein the arch areas of the respective articles of the set share a same cross-sectional profile,
    wherein the heel areas of the respective articles of the set have different depths D so that the heel is differently suspended from a bottom of the heel area,
    wherein the arch area and the heel area are adapted, configured and cooperate to suspend the heel within the heel area so that (i) the heel is not in contact with the article and (ii) a calcaneal spur of the heel is spacedly disposed from a bottom of the recess of the heel area.

2. The set of claim 1, wherein each article of the set further comprises a forefoot area.

3. The set of claim 1, wherein each article is configured so as to be integrated into the shoe.

4. The set of claim 1, wherein the set comprises at least three articles, and wherein the respective depths D of the articles ranges between about 10 mm and 35 mm.

5. A method of spacedly suspending a heel within a podiatric article so as to minimally traumatize a calcaneal spur, comprising:
    providing a set of podiatric articles each of which is placeable into a respective one of a pair of shoes, each article of the set including:
        an arch area with a cross-sectional profile; and
        a heel area having a depth D and a concave shape that provides a round recess that is adapted, configured, and dimensioned to receive a heel, wherein
        (i) the arch areas of the respective articles of the set share a same cross-sectional profile,
        (ii) the heel areas of the respective articles of the set have different depths D so that the heel is differently suspended from a bottom of the heel area, and
        (iii) the arch area and the heel area are adapted, configured and cooperate to suspend the heel within the heel area so that (i) the heel is not in contact with the article and (ii) a calcaneal spur of the heel is spacedly disposed from a bottom of the recess of the heel area;
    selecting, empirically, one or more of the articles that will suspend the heel via the cooperation of the heel and arch areas of the articles, based on an apparent maximal comfort and an apparent minimal pain resulting from potential heel contact with the article; and
    identifying one of the selected articles that provides maximum comfort and minimal pain when the heel is suspended in the heel area via the cooperation of the heel and arch areas of the one article.

6. The set of claim 5, wherein each article of the set further comprises a forefoot area.

7. The set of claim 5, wherein each article is configured so as to be integrated into the shoe.

8. The set of claim 5, wherein the set comprises at least three articles, and wherein the respective depths D of the articles ranges between about 10 mm and 35 mm.

* * * * *